United States Patent
Simmons et al.

(10) Patent No.: US 10,328,185 B2
(45) Date of Patent: Jun. 25, 2019

(54) APPARATUS, METHOD, AND SYSTEM FOR CONTROLLING NEGATIVE-PRESSURE TREATMENT

(71) Applicant: KCI Licensing, Inc., San Antonio, TX (US)

(72) Inventors: Tyler H. Simmons, San Antonio, TX (US); Reuben Walter Edgar, Jr., San Antonio, TX (US); Kevin Higley, San Antonio, TX (US); Loren Francis, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 522 days.

(21) Appl. No.: 15/080,555

(22) Filed: Mar. 24, 2016

(65) Prior Publication Data

US 2016/0287763 A1 Oct. 6, 2016

Related U.S. Application Data (60) Provisional application No. 62/143,515, filed on Apr. 6, 2015.

(51) Int. Cl.
*A61M 1/00* (2006.01)
*A61F 13/00* (2006.01)
*A61F 13/02* (2006.01)

(52) U.S. Cl.
CPC ..... *A61M 1/0031* (2013.01); *A61F 13/00068* (2013.01); *A61F 13/0216* (2013.01);
(Continued)

(58) Field of Classification Search
CPC .............. A61M 1/0025; A61M 1/0031; A61M 1/0088; A61M 2205/18;
(Continued)

(56) References Cited

U.S. PATENT DOCUMENTS 1,355,846 A 10/1920 Rannells
2,547,758 A 4/1951 Kelling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
(Continued)

*Primary Examiner* — Benjamin J Klein (57) ABSTRACT

In one example embodiment, an apparatus for providing negative-pressure therapy may comprise a negative-pressure source, a pressure sensor, and a control valve. The negative-pressure source may be configured to be fluidly coupled to a distribution component. The control valve may be fluidly coupled to the pressure sensor and configured to be selectively coupled to the negative-pressure source, the distribution component, or both. A controller may also be configured to operate the control valve to selectively couple the pressure sensor to at least one of the negative-pressure source and the distribution component through the control valve, and the pressure sensor may provide a feedback signal to the controller indicative of pressure in a feedback path associated with the position of the control valve. The controller may also be configured to operate the negative-pressure source based on the feedback signal.

32 Claims, 2 Drawing Sheets

(52) U.S. Cl.
CPC ........ *A61M 1/0025* (2014.02); *A61M 1/0088* (2013.01); *A61M 2205/18* (2013.01); *A61M 2205/3331* (2013.01); *A61M 2205/3344* (2013.01)

(58) Field of Classification Search
CPC ... A61M 2205/3331; A61M 2205/3344; A61F 13/00068; A61F 13/0216
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0042059 A1* | 2/2010 | Pratt .................. A61M 1/0031 604/318 |
| 2010/0280422 A1* | 11/2010 | Hartwell ............. A61M 1/0031 601/6 |
| 2012/0271257 A1 | 10/2012 | Coulthard et al. |
| 2013/0296816 A1* | 11/2013 | Greener ............. A61M 1/0031 604/320 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |

(56) References Cited

FOREIGN PATENT DOCUMENTS

| | | |
|---|---|---|
| WO | 99/13793 A1 | 3/1999 |
| WO | 2013/078214 A1 | 5/2013 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), page 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion corresponding to PCT/US2016/024115, dated Jul. 1, 2016.

\* cited by examiner

APPARATUS, METHOD, AND SYSTEM FOR CONTROLLING NEGATIVE-PRESSURE TREATMENT

RELATED APPLICATION

This application claims the benefit, under 35 USC § 119(e), of the filing of U.S. Provisional Patent Application Ser. No. 62/143,515, entitled "APPARATUS, METHOD, & SYSTEM FOR CONTROLLING NEGATIVE-PRESSURE TREATMENT" filed Apr. 6, 2015, which is incorporated herein by reference for all purposes.

TECHNICAL FIELD

The invention set forth in the appended claims relates generally to tissue treatment systems and more particularly, but without limitation, to methods and apparatuses for providing and controlling negative-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

BRIEF SUMMARY

New and useful systems, apparatuses, and methods for controlling negative-pressure treatment are set forth in the appended claims. Illustrative embodiments are also provided to enable a person skilled in the art to make and use the claimed subject matter.

For example, in some embodiments, a single pressure sensor can be connected to at least two feedback paths via a solenoid valve. The feedback paths may be in fluid communication with a negative-pressure source and a dressing or other distribution component. A therapy unit may have a controller programmed or otherwise configured to switch the solenoid valve on and off to measure pressure from each of the feedback paths. When switching from a feedback path for a negative-pressure source to a feedback path for a dressing, a brief venting of the feedback path for the dressing to atmospheric pressure may improve the accuracy of the pressure sensor. In some embodiments, the same venting may be used to purge the feedback path of fluid periodically.

More generally, an example embodiment of an apparatus for providing negative-pressure therapy is described herein that may comprise a negative-pressure source, a pressure sensor, and a control valve. The negative-pressure source may be fluidly coupled or configured to be fluidly coupled to a distribution component. The control valve may be fluidly coupled to the pressure sensor and configured to be selectively coupled to the negative-pressure source, the distribution component, or both. A controller may also be coupled to the control valve and to the pressure sensor, and the controller can be configured to operate the control valve to selectively couple the pressure sensor to at least one of the negative-pressure source and the distribution component through the control valve, and the pressure sensor may provide a feedback signal to the controller indicative of pressure in a feedback path associated with the position of the control valve. The controller can correlate the feedback signal with the position of the control valve to associate the feedback signal with a feedback path. In more specific embodiments, the control valve may be or may comprise one or more electromechanical valves configured to receive a control signal from a controller. The controller may also be coupled to the negative-pressure source, and be configured to operate the negative-pressure source based on the feedback signal.

In some embodiments, the control valve is normally closed between the pressure sensor and the negative-pressure source, and the controller may periodically open the control valve between the pressure sensor and the negative-pressure source. The control valve may also be normally open between the pressure sensor and the distribution component in some example embodiments, and the controller may periodically switch the position of the control valve between the negative-pressure source and the distribution component. For example, the controller may open the control valve between the pressure sensor and the negative-pressure source, and close the control valve between the pressure sensor and the distribution component.

The control valve may comprise at least two inlet ports and one outlet port in some embodiments. For example, the control valve may comprise a first inlet port configured to be fluidly coupled to a distribution component, and a second inlet port fluidly coupled to a negative-pressure source. An outlet port may be fluidly coupled to the pressure sensor. In some embodiments, the control valve may comprise more than one valve. For example, a first inlet port may be associated with a first valve, and a second inlet port may be associated with a second valve.

Alternatively or additionally, other example embodiments may include an apparatus comprising a negative-pressure source, a pressure sensor, and one or more feedback paths configured to pneumatically couple the pressure sensor to a distribution component and to the negative-pressure source. A control valve may be configured to selectively couple the pressure sensor to at least one of the feedback paths. The apparatus may further include a controller coupled to the negative-pressure source, the control valve, and the pressure sensor. The controller can be configured to operate the control valve, sample a signal from the pressure sensor indicative of pressure measured by the pressure sensor, and operate the negative-pressure source based on the signal. In some embodiments, operating the negative-pressure source may include diagnosing one or more operating conditions based on the signal and activating an alert indicative of the operating condition.

Example methods for controlling negative-pressure treatment are also described herein, wherein some example embodiments of the methods may be implemented in a controller coupled to a negative-pressure source. For example, some embodiments may include sampling a signal from a pressure sensor indicative of an operating parameter measured by the pressure sensor, and periodically operating a control valve to switch the operating parameter measured by the pressure sensor. A negative-pressure source may be operated based on the signal.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
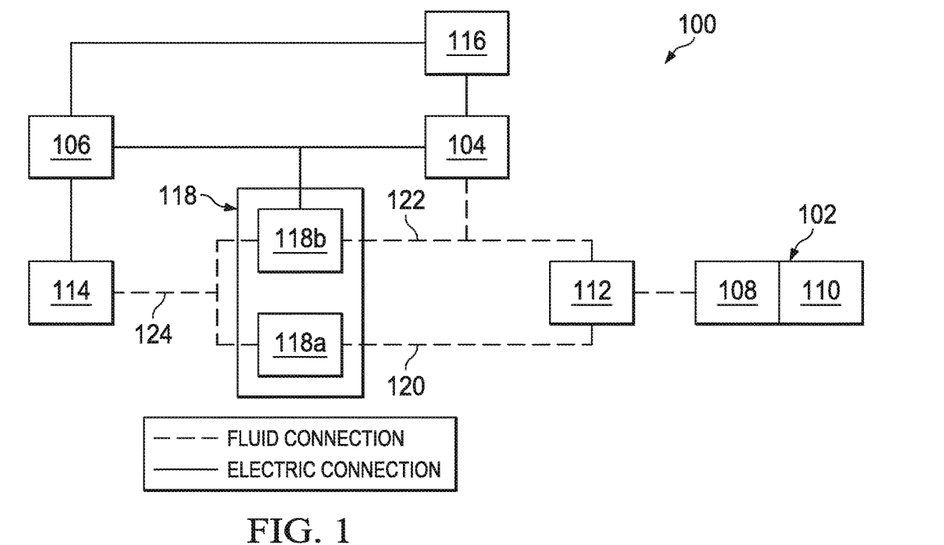
FIG. 1 is a functional block diagram of an example embodiment of a therapy system that can provide negative-pressure therapy to a tissue site in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

The therapy system 100 may include a negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1. A dressing generally includes a cover and a tissue interface. The dressing 102, for example, may include a cover 108 and a tissue interface 110. A controller, such as a controller 106, may also be coupled to the negative-pressure source 104.

In some embodiments, a dressing interface may facilitate coupling negative-pressure source 104 to the dressing 102. For example, such a dressing interface may be a T.R.A.C.® Pad or Sensa T.R.A.C.® Pad available from KCI of San Antonio, Tex. The therapy system 100 may optionally include a fluid container, such as a container 112, coupled to the dressing 102 and to the negative-pressure source 104.

Additionally, the therapy system 100 may include sensors to measure operating parameters and provide feedback signals to the controller 106 indicative of the operating parameters. As illustrated in FIG. 1, for example, the therapy system 100 may include a pressure sensor 114 and an electric sensor 116 coupled to the controller 106. The pressure sensor 114 may also be coupled or configured to be coupled to a distribution component and to the negative-pressure source 104. For example, the pressure sensor 114 may be fluidly coupled to the dressing 102 and to the negative-pressure source 104 through a control valve 118, as illustrated in the example embodiment of FIG. 1. The control valve 118 is also preferably coupled to the controller 106.

In some embodiments, the control valve 118 may be a four-way valve, but in other embodiments may comprise more than one valve, such as a combination of two-way and/or three-way valves. For example, as illustrated in FIG. 1, the control valve 118 may comprise a first valve 118a and a second valve 118b. In some embodiments the first valve 118a and the second valve 118b may be combined in a single housing, but in other embodiments the first valve 118a and the second valve 118b may have separate housings. The first valve 118a and the second valve 118b are each preferably a three-way valve, but either or both may be two-way valves in some embodiments.

Components of the therapy system 100 may be coupled to each other to provide a path for transferring fluids (i.e., liquid and/or gas) between the components. In some embodiments, for example, components may be fluidly coupled through a tube. A "tube," as used herein, broadly refers to a tube, pipe, hose, conduit, or other fluid conductor with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, optical, or chemical coupling (such as a chemical bond) in some contexts.

In general, components of the therapy system 100 may be coupled directly or indirectly. For example, the negative-pressure source 104 may be directly coupled to the controller 106, and may be indirectly coupled to the dressing 102 through the container 112.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a negative-pressure source, and conversely, the term "upstream" implies something relatively further away from a negative-pressure source. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as the controller 106, the pressure sensor 114, the electrical sensor 116, processing units, alarm indicators, memory, databases, software, display devices, or user interfaces that further facilitate negative-pressure therapy. A negative-pressure source may also have one or more supply ports configured to facilitate coupling and de-coupling the negative-pressure source to one or more distribution components.

The tissue interface 110 can be generally adapted to contact a tissue site. The tissue interface 110 may be partially or fully in contact with the tissue site. If the tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites.

In some embodiments, the tissue interface 110 may be a manifold. A "manifold" in this context generally includes any substance or structure providing a plurality of pathways adapted to collect or distribute fluid across a tissue site under pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some embodiments, a manifold may also include closed cells to contain or direct distribution of fluid through open cells. A manifold may also be molded to provide surface projections that define interconnected fluid pathways in some embodiments. In some illustrative embodiments, a manifold may be a porous foam material having interconnected cells or pores adapted to uniformly (or quasi-uniformly) distribute negative pressure to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 110 may further promote granulation at a tissue site when pressure within the sealed therapeutic environment is reduced. For example, any or all of the surfaces of the tissue interface 110 may have an uneven, coarse, or jagged profile that can induce microstrains and stresses at a tissue site if negative pressure is applied through the tissue interface 110.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 108 may provide a bacterial barrier and protection from physical trauma. The cover 108 may also be constructed from a material that can reduce evaporative losses and provide a fluid seal between two components or two environments, such as between a therapeutic environment and a local external environment. The cover 108 may be, for example, an elastomeric film or membrane that can provide a seal adequate to maintain a negative pressure at a tissue site for a given negative-pressure source. The cover 108 may have a high moisture-vapor transmission rate (MVTR) in some applications. For example, the MVTR may be at least 300 g/m^2 per twenty-four hours in some embodiments. In some example embodiments, the cover 108 may be a polymer drape, such as a polyurethane film or sheet that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 108 may be coated with an acrylic adhesive having a coating weight between 25-65 g.s.m. Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 106, may be a microprocessor or computer programmed to operate one or more components of the therapy system 100, such as the negative-pressure source 104 and the control valve 118. In some embodiments, for example, the controller 106 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 110, for example. The controller 106 is also preferably configured to receive one or more input signals, such as a feedback signal, and programmed to modify one or more operating parameters based on the input signals.

Sensors, such as the pressure sensor 114 or the electric sensor 116, are generally known in the art as any apparatus operable to detect or measure a physical phenomenon or property, and generally provide a signal indicative of the phenomenon or property that is detected or measured. For example, the pressure sensor 114 and the electric sensor 116 may be configured to measure one or more operating parameters of the therapy system 100. In some embodiments, the pressure sensor 114 may be a transducer configured to measure pressure in a pneumatic pathway and convert the measurement to a signal indicative of the pressure measured. In some embodiments, for example, the pressure sensor 114 may be a piezoresistive strain gauge. The electrical sensor 116 may optionally measure operating parameters of the negative-pressure source 104, such as the voltage or current, in some embodiments. Preferably, the signals from the pressure sensor 114 and the electric sensor 116 are suitable as an input signal to the controller 106, but some signal conditioning may be appropriate in some embodiments. For example, the signal may need to be filtered or amplified before it can be processed by the controller 106. Typically, the signal is an electrical signal, but may be represented in other forms, such as an optical signal.

A valve, such as the control valve 118 of FIG. 1, generally includes any apparatus that is operable to control the flow of a fluid through a fluid conductor. For example, the control valve 118 may be a directional control valve configured to change the direction of fluid flow, stop fluid flow, release fluid flow, distribute fluid, or mix fluid. A valve typically comprises a housing, a fluid passage between to two or more ports, and an obstruction moveable between discreet positions to open or close the fluid passage between ports in various combinations. In some valves, the obstruction may be referred to as a "seal," a "valve member" or a "disc." For convenience, the position of the obstruction and the resulting fluid connections between ports may be referred to herein as the position of the valve, and moving a valve from one position to another may be referred to herein as "switching" the valve.

In some embodiments, a valve may also include an actuator configured to move the obstruction between positions, or an actuator may be the obstruction. For example, an actuator may be configured to accept energy and produce movement of a seal to open or close the fluid paths between ports in various combinations to change valve functions. If a valve includes an actuator, applying energy to the actuator sufficient to move an obstruction from one position to another may be referred to as "actuating" the valve. A first position of the valve without energy applied to an actuator may be referred to as the "normal" position. A second position with energy applied to an actuator may be referred to as an "activated" position. Some valves may have more than one activated position.

The control valve 118 preferably comprises an actuator, at least two ports, and at least one fluid path between the ports. In the embodiment of FIG. 1, the control valve 118 has at least two inlet ports and two outlet ports. The control valve 118 may also include exhaust ports, which may be in fluid communication with the ambient atmosphere.

In some embodiments, the control valve 118 may include an actuator configured to accept energy in the form of a signal from a controller, such as the controller 106, and convert the signal into movement of a seal between a first position and a second position, to open and close ports, respectively. In some embodiments, opening and closing a port may also implicitly open and close a fluid passage through the control valve 118.

As illustrated in the example embodiment of FIG. 1, the control valve 118 may comprise inlet ports coupled to a first pneumatic feedback path 120 and a second pneumatic feedback path 122. Each of the feedback path 120 and the feedback path 122 may couple the respective inlet ports of the control valve 118 to one or more components of the therapy system, and may comprise more than one segment. For example, the feedback path 120 may comprise one or more segments between the first valve 118a and the container 112 to pneumatically couple the container 112 to the control valve 118, and the feedback path 122 may comprise one or more segments between the second valve 118b and the negative-pressure source 104 to pneumatically couple the control valve 118 to the negative-pressure source 104. In some embodiments, such as in the example embodiment of FIG. 1, the feedback path 120 may also include a segment through the container 112, and between the container 112 and the dressing 102, to pneumatically couple the inlet port P1 to the dressing 102. Moreover, some part of the feedback path 120 may comprise a lumen through a multi-lumen fluid conductor. For example, a multi-lumen tube may fluidly couple the container 112 to the dressing 102. In such an example embodiment, the feedback path 120 may include one lumen in the tube, and the feedback path. 122 may include another lumen in the tube. In other embodiments, the container 112 may be omitted or the feedback path 120 may bypass or circumvent the container 112.

The control valve 118 may have one or more outlet ports pneumatically coupled to the pressure sensor 114, as illustrated in the example embodiment of FIG. 1. In some embodiments, for example, outlet ports may be coupled to the pressure sensor 114 through a combined or merged feedback path, such as a third pneumatic feedback path 124 illustrated in FIG. 1. In other embodiments the pneumatic connections between the control valve 118 and the pressure sensor 114 may be separate.

In some embodiments, the control valve 118 may be normally open between the feedback path 120 and the feedback path 124, fluidly coupling the pressure sensor 114 to the feedback path 120 through the control valve 118. The control valve 118 may be normally closed between the feedback path 122 and the feedback path 124, terminating the feedback path 122 at the control valve 118 or, in some embodiments, fluidly coupling to the feedback path 122 to an exhaust port.

In some embodiments, the control valve 118 may be or may comprise one or more electromechanical valves operated by electric current. For example, the first valve 118a and the second valve 118b may each be a solenoid valve having an actuator controlled by an electric current through a solenoid. In some embodiments, the electric current may be provided by the controller 106 in the form of a control signal.

Figure 2:
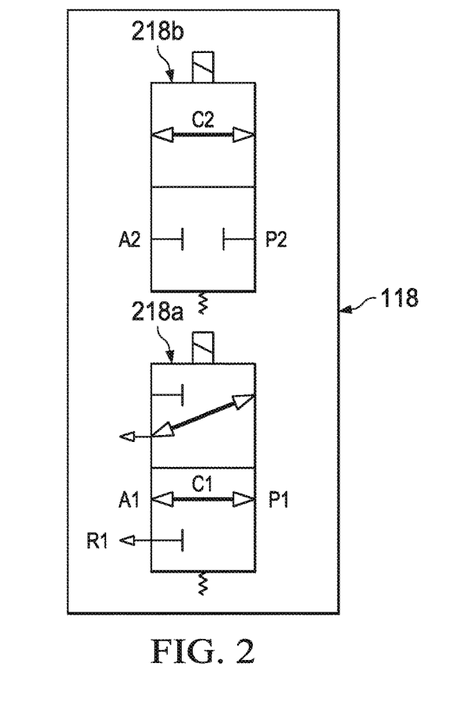
FIG. 2 is a schematic diagram illustrating additional details that may be associated with an example embodiment of a control valve in the therapy system of FIG. 1.

FIG. 2 is a schematic diagram illustrating additional details that may be associated with one example embodiment of the control valve 118. In the example embodiment of FIG. 2, the control valve 118 comprises a first valve 218a and a second valve 218b. The first valve 218a may be a three-port, two-position (3/2) solenoid valve, which may be illustrative of an example embodiment of the first valve 118a of FIG. 1. A 3/2 solenoid valve sold by Parker Hannifin Corp. under the trade name of X-VALVE and having a part number of 912-000001-031 may be preferable or suitable in some embodiments. The second valve 218b may be a two-port, two-position (2/2) solenoid valve, which may be illustrative of an example embodiment of the second valve 118b of FIG. 1.

A normal position of each valve is illustrated in the lower box of each valve diagram, and an activated position is illustrated in the upper box. In FIG. 2, for example, the first valve 218a is normally open between an inlet port P1 and an outlet port A1, indicated by a fluid channel C1 fluidly coupling the inlet port P1 to the outlet port A1. If actuated, the first valve 218a can close the outlet port A1 and may optionally connect the inlet port P1 to an exhaust port R1 The second valve 218b may be normally closed between an inlet port P2 and an outlet port A2, and can open the outlet port A2 to couple the inlet port P2 and the outlet port A2 through a fluid channel C2 if actuated.

In some embodiments, the inlet port P1 and the inlet port P2 may be fluidly coupled to feedback paths in the therapy system 100. For example, the inlet port P1 may be coupled to the feedback path 120 of FIG. 1, and the inlet port P2 may be coupled to the feedback path 122 in some embodiments. The outlet port A1 and the outlet port A2 may also be fluidly coupled to a feedback path, such as the feedback path 124 of FIG. 1.

Figure 3:
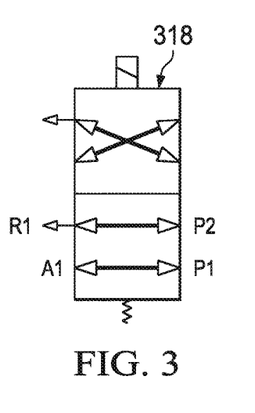
FIG. 3 is a schematic diagram illustrating additional details that may be associated with another example embodiment of a control valve in the therapy system of FIG. 1.

FIG. 3 is a schematic diagram illustrating additional details that may be associated with another example embodiment of the control valve 118. In the example embodiment of FIG. 3, the control valve 118 may comprise or consist of a four-port, two-position (4/2) valve, such as the valve 318. In FIG. 3, for example, the valve 318 may be normally open between the inlet port P1 and the outlet port A1, and normally open between the inlet port P2 and the exhaust port R1. In other embodiments, the valve 318 may be normally closed between the inlet port P2 and the exhaust port R1. If actuated, the valve 318 can switch the fluid paths between the ports to fluidly couple the inlet port P1 to the exhaust port R1 and to fluidly couple the inlet port P2 to the outlet port A1.

In operation, the tissue interface 110 may be placed within, over, on, or otherwise proximate to a tissue site. The cover 108 may be placed over the tissue interface 110 and sealed to tissue near the tissue site. For example, the cover 108 may be sealed to undamaged epidermis peripheral to a tissue site. The negative-pressure source 104 may be fluidly coupled to the tissue interface 110 through the cover 108. In some embodiments, the negative-pressure source 104 may also be fluidly coupled to one or more other intermediate components, such as the container 112. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 110 in the sealed therapeutic environment can induce macrostrain and microstrain in the tissue site, as well as remove exudates and other fluids from the tissue site, which can be collected in container 112 and disposed of properly.

While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −25 mm Hg (−3.3 kPa) and −200 mm Hg (−26.7 kPa). Negative pressure may also be varied or intermittent according to therapeutic requirements.

In the example embodiment of FIG. 1, the controller 106 may be programmed or otherwise configured to switch the control valve 118, selectively coupling the pressure sensor 114 to at least one of the feedback path 120 and the feedback path 122. For example, in some embodiments, the control valve 118 may be normally open between the feedback path 120 and the feedback path 124 so that the pressure sensor 114 is pneumatically coupled to the feedback path 120, and the control valve 118 may be normally closed between the feedback path 122 and the feedback path 124. The controller 106 may be programmed to switch the control valve 118, pneumatically coupling the pressure sensor 114 to the feedback path 122. In some embodiments, the control valve 118 also may close the feedback path 120 if the control valve 118 is switched. In other embodiments, the pressure sensor 114 may remain coupled to the feedback path 120 if the control valve is switched. In some embodiments, the controller 106 may actuate the control valve 118 at a time interval of five minutes. The time interval may vary according to operator preference or prescribed therapy, but the time interval may be configurable and is preferably at least two minutes and less than ten minutes.

In some embodiments, the feedback path 120 may also be vented or purged through the control valve 118. For example, in the embodiment illustrated in FIG. 2, the feedback path 120 may be vented through the exhaust port R1 if the controller 106 actuates the first valve 218a.

Additionally or alternatively, the controller 106 of FIG. 1 may be programmed or otherwise configured to merge the feedback path 120 and the feedback path 122. For example, in some embodiments, the controller 106 may be programmed to periodically open the first valve 118a and the second valve 118b simultaneously for a configurable time interval.

The controller 106 may also be programmed or otherwise configured to sample feedback signals from the pressure sensor 114 indicative of pressure in the pneumatic feedback path coupled to the pressure sensor 114. The controller 106 may also be configured to correlate feedback signals from the pressure sensor 114 with the position of the control valve 118 to associate the feedback signals with a feedback path. For example, in the example embodiment of FIG. 1, the controller 106 may receive a signal from the pressure sensor 114 with the control valve 118 in a position indicative of pressure in the feedback path 124. In some embodiments, the frequency of the sampling may be sufficiently high to approximate continuous monitoring of the pressure in the feedback path 124. Venting may be advantageous for improving accuracy of signals from the pressure sensor 114, particularly when switching from the feedback path 122 to the feedback path 120. The same venting interval may also be used to purge the feedback path 120 periodically.

The pressure in the feedback path 124 generally depends on the position of the control valve 118, and the controller 106 can be configured to correlate a signal from the pressure sensor 114 with a position of the control valve 118. For example, the signal may be indicative of pressure in the tissue interface 110 in some embodiments if the control valve 118 pneumatically couples the pressure sensor 114 to the feedback path 120. The pressure in the feedback path 124 may also be indicative of pressure from the negative-pressure source 104 if the control valve 118 pneumatically couples the pressure sensor 114 to the feedback path 122. In some embodiments, the controller 106 may also be configured to open all inlet ports of the control valve 118, and the signal from the pressure sensor 114 may be indicative of a merged or combined pressure from the feedback path 120 and the feedback path 124.

The controller 106 may also be configured to manage negative-pressure therapy based on signals from the pressure sensor 114 and the electrical sensor 116. For example, the controller 106 can be programmed or otherwise configured to manage pressure delivered to the dressing 102. In some embodiments, for example, the controller 106 may be programmed or otherwise configured to compare a signal from the pressure sensor 114 to a set-point, and modify the power or other input applied to the negative-pressure source 104 to drive the signal to the set-point based on the comparison. The set-point may be a target pressure prescribed for therapy, or a safety-threshold, for example. In some embodiments, the controller 106 can operate the control valve 118 to couple the feedback path 120 to the feedback path 124, and receive a signal from the pressure sensor 114 indicative of pressure in the dressing 102, or more specifically, pressure in the tissue interface 110. Such a signal from the pressure sensor 114 indicative of pressure in the dressing 102 may be illustratively referred to herein as a "distribution signal," which the controller 106 may correlate or associate with one position of the control valve 118. For example, the controller 106 may correlate the normal position of the control valve with the distribution signal. The controller 106 can compare the distribution signal received from the pressure sensor 114 with a target pressure and generate a control signal based on the comparison. The control signal can be sent to the negative-pressure source 104 to modify the voltage or current applied to the negative-pressure source 104. For example, the control signal can cause the negative-pressure source 104 to decrease pressure if the distribution signal is higher than the target pressure, or can increase pressure if the distribution signal is less than the target pressure or a safety threshold.

In some embodiments, the controller 106 can also be programmed or otherwise configured to diagnose operating conditions, including operating anomalies, based on the operating parameters measured by the pressure sensor 114, the electrical sensor 116, or both. For example, in some embodiments, the control valve 118 may be normally open between the feedback path 120 and the feedback path 124, preferably excluding the feedback path 122, and the controller 106 may be configured to regularly sample a distribution signal from the pressure sensor 114. The controller can periodically actuate the control valve 118 to close the feedback path 120, and open the feedback path 122 to the feedback path 124. If the feedback path 120 is closed and the feedback path 122 is coupled to the feedback path 124, the controller 106 can receive a pressure signal from the pressure sensor 114 indicative of the pressure from the negative-pressure source 104, for example. Such a pressure signal from the pressure sensor 114 indicative of pressure from the negative-pressure source 104 may be illustratively referred to herein as a "supply signal," which may be correlated or associated with a position of the control valve. For example, the controller 106 may correlate an actuated position of the control valve 118 with the supply signal. The controller 106 may be configured to compare a supply signal to a distribution signal to diagnose a fluid leak. For example, in some embodiments, a supply signal that is lower than a distribution signal may be indicative of a leak in the dressing 102 or a leak in a fluid path between the negative-pressure source 104 and the dressing 102. The controller 106 may also be configured to activate an alert indicative of the fluid leak.

In some embodiments, the controller 106 may also be configured to infer the performance of the negative-pressure source 104 based on the voltage or current measured by the electrical sensor 116. A signal from the electric sensor 116 based on voltage or current and indicative of pressure from the negative-pressure source 104 may be illustratively referred to herein as a "power signal." The power signal may be compared with a supply signal, a distribution signal, or both to detect operating anomalies in the therapy system 100 based on the responsiveness of the signal from the pressure sensor 114. For example, in some embodiments, the controller 106 may be configured to diagnose a fluid leak by comparing the responsiveness of a supply signal or a distribution signal from the pressure sensor 114 to a change in a power signal over a fixed time interval.

In some embodiments, the controller 106 may be configured to merge the feedback path 120 and the feedback path 122 for additional or alternative diagnosis. For example, if a distribution signal indicates pressure in the dressing 102 is above a target pressure, the controller 106 may actuate the control valve 118 to merge the feedback path 120 and the feedback path 122. In this context, the pressure sensor 114 can provide a pressure signal indicative of the merged pressure from the feedback path 120 and the feedback path 122. Such a pressure signal indicative of the merged pressure may be illustratively referred to herein as a "performance signal," which may be correlated or associated with a position of the control valve. For example, the controller 106 may correlate the performance signal with an actuated position of the control valve 118 in some embodiments. The performance signal can be compared to the distribution signal to diagnose operating conditions such as low negative-pressure in the dressing 102. For example, if the performance signal is greater than the distribution signal, the controller 106 can compare the difference to a tolerance parameter, which can be programmed into the controller 106 or configured by an operator. If the difference is less than the tolerance parameter, the controller 106 may activate an alert signal indicative of a mechanical malfunction of the negative-pressure source 104 or a leak in the fluid path between the negative-pressure source 104 and the dressing 102, for example. If the difference is greater than the tolerance parameter, the controller 106 may generate an alert signal indicating an obstruction in the fluid path between the negative-pressure source 104 and the dressing 102. Such an obstruction may include a full canister or debris in a tube, for example. If the performance signal is less than the distribution signal, the controller may generate an alert signal indicating an obstruction in the fluid path between the dressing 102 and the pressure sensor 114, such as in the feedback path 120, for example.

Additionally or alternatively, the controller 106 may be configured to detect fluid obstructions, such as a full canister or debris in a tube, based on a similar comparison. Mechanical failures of the negative-pressure source 104 may also be diagnosed by the controller 106 in some embodiments. For example, the controller 106 may diagnose a failure in the negative-pressure source 104 if the current draw and the voltage applied to the negative-pressure source 104 both exceed a threshold value. The controller 106 may also be configured to operate other components if certain conditions are diagnosed. For example, the controller 106 may interrupt the negative-pressure source 104 or activate an alarm if a fluid leak or obstruction is diagnosed.

Figure 4:
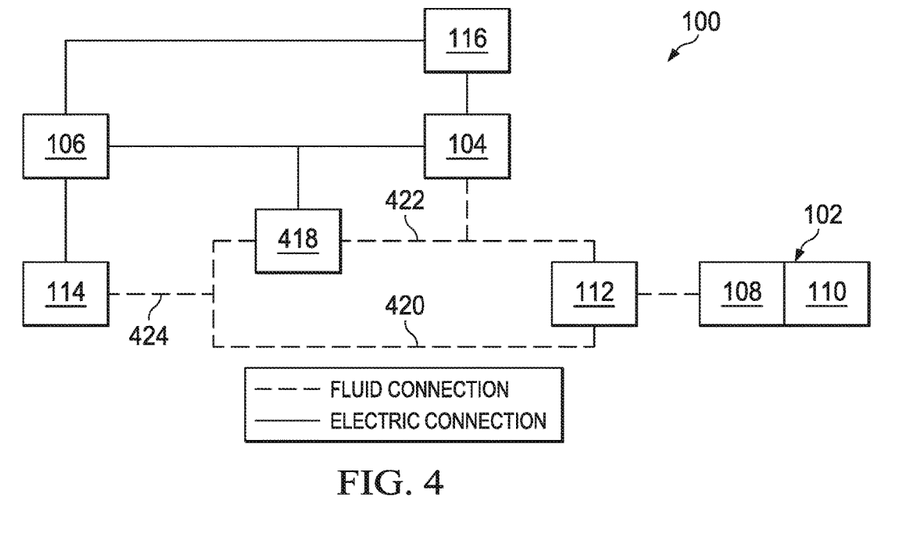
FIG. 4 is a functional block diagram of another example embodiment of a therapy system that can provide negative-pressure therapy to a tissue site in accordance with this specification.

FIG. 4 is a functional block diagram of another example embodiment of the therapy system 100. In the example embodiment of FIG. 4, the therapy system 100 may also include or be configured to be coupled to the dressing 102. For example, the negative-pressure source 104 may be coupled or configured to be coupled to the dressing 102. The controller 106 may also be coupled to the negative-pressure source 104 in this example embodiment. The therapy system 100 of FIG. 4 may optionally include a fluid container, such as the container 112, coupled to the dressing 102 and to the negative-pressure source 104.

In the example embodiment of FIG. 4, the therapy system 100 may also include sensors, such as the pressure sensor 114 and the electric sensor 116, to measure operating parameters and provide feedback signals to the controller 106 indicative of the operating parameters. The pressure sensor 114 is also preferably coupled or configured to be coupled to the dressing 102 and the negative-pressure source 104 through a pneumatic connection. For example, the pressure sensor 114 may be fluidly coupled to the dressing 102 through a pneumatic feedback path 420, as illustrated in the example embodiment of FIG. 4. In some embodiments, the pressure sensor 114 may be directly coupled to the dressing 102, but the pneumatic feedback path 420 may include the container 112 in other embodiments. The pressure sensor 114 may also be fluidly coupled to the negative-pressure source 104 through a control valve 418, as illustrated in the example embodiment of FIG. 4. The control valve 418 is preferably coupled to the controller 106. In the example embodiment of FIG. 4, the control valve 418 preferably comprises at least two-ports. For example, as illustrated in FIG. 4, the control valve 418 may be a two-port, two-position (2/2) electromechanical valve, such as a solenoid valve, having an inlet port, an outlet port, and a fluid path between the inlet port and the outlet port.

The control valve 418 may be pneumatically coupled to the negative-pressure source 104 in some embodiments, as illustrated in the example embodiment of FIG. 4, to provide a pneumatic feedback path 422 from the negative-pressure source 104 to an inlet port of the control valve 418. An outlet port of the control valve 418 can be coupled to the pressure sensor 114 through a pneumatic feedback path 424. In some embodiments, the control valve 418 may be normally closed between the feedback path 422 and the feedback path 424, and may be actuated by an electric current, such as a control signal from the controller 106, to fluidly couple the feedback path 422 and the feedback path 424.

As illustrated in the example embodiment of FIG. 4, the feedback path 420 and the feedback path 424 may be merged or otherwise fluidly coupled between the pressure sensor 114 and the control valve 418.

In operation, the pressure sensor 114 may regularly measure or otherwise sample pressure from the feedback path 420. In some embodiments, the frequency of the sampling may be sufficiently high to approximate continuous monitoring of the pressure in the feedback path 420. In some embodiments, the controller 106 can also be programmed or otherwise configured to open the control valve 418, which can merge the feedback path 420 with the feedback path 422.

The controller 106 of FIG. 4 can also be programmed or otherwise configured to manage or diagnose operating conditions based on the operating parameters measured by the pressure sensor 114, the electrical sensor 116, or both, substantially as described above. In some embodiments, the controller 106 may be configured to open the control valve 418 for additional or alternative diagnosis.

For example, if a distribution signal indicates pressure in the dressing 102 is above a target pressure, the controller 106 may open the control valve 418 to merge the feedback path 420 and the feedback path 422. In this context, the pressure sensor 114 can provide a performance signal indicative of the merged pressure from the feedback path 420 and the feedback path 422. The performance signal can be compared to the distribution signal to diagnose operating conditions such as low negative-pressure in the dressing 102. For example, if the performance signal is greater than the distribution signal, the controller 106 can compare the difference to a tolerance parameter, which can be programmed into the controller 106 or configured by an operator. If the difference is less than the tolerance parameter, the controller 106 may generate an alert signal indicative of a mechanical malfunction of the negative-pressure source 104 or a leak in the fluid path between the negative-pressure source 104 and the dressing 102, for example. If the difference is greater than the tolerance parameter, the controller 106 may generate an alert signal indicating an obstruction in the fluid path between the negative-pressure source 104 and the dressing 102. Such an obstruction may include a full canister or debris in a tube, for example. If the performance signal is less than the distribution signal, the controller may generate an alert signal indicating an obstruction in the fluid path between the dressing 102 and the pressure sensor 114, such as in the feedback path 420, for example.

The systems, apparatuses, and methods described herein may provide significant advantages. Among other advantages, one pressure sensor can be used in a therapy unit while maintaining the functionality of two pressure sensors. For example, in some embodiments, a single pressure sensor can be connected to both a negative-pressure source and a feedback path of a therapy unit. Eliminating a second pressure sensor and associated hardware can reduce the cost and size of a main board, which can also significantly simplify board design and reduce manufacturing cost of a therapy unit. Additionally, errors from faulty or improperly calibrated sensors can be reduced by using a single pressure sensor.

While shown in a few illustrative embodiments, a person having ordinary skill in the art will recognize that the systems, apparatuses, and methods described herein are susceptible to various changes and modifications. For example, the configuration of the control valve 118 is not limited to the specific examples described herein, and other configurations that can selectively couple more than one input to a single pressure sensor are contemplated. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In some configurations, the controller 106 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for providing negative-pressure therapy, the apparatus comprising:
   a negative-pressure source configured to be fluidly coupled to a distribution component;
   a control valve fluidly coupled to the negative-pressure source and configured to be fluidly coupled to the distribution component;
   a pressure sensor fluidly coupled to the control valve, the control valve being between the pressure sensor and the negative-pressure source and the distribution component; and
   a controller coupled to the control valve and to the pressure sensor, the controller configured to:
      actuate the control valve to selectively couple at least one of the negative-pressure source and the distribution component to the pressure sensor through the control valve, and
      receive a feedback signal from the pressure sensor.

2. The apparatus of claim 1, wherein the control valve is normally closed between the pressure sensor and the negative-pressure source.

3. The apparatus of claim 1, wherein:
   the control valve is normally closed between the pressure sensor and the negative-pressure source; and
   the controller is configured to periodically open the control valve between the pressure sensor and the negative-pressure source.

4. The apparatus of claim 1, wherein:
   the control valve comprises an inlet port fluidly coupled to the negative-pressure source and an outlet port fluidly coupled to the pressure sensor;
   the control valve is normally closed between the pressure sensor and the negative-pressure source; and
   the controller is configured to periodically open the control valve between the pressure sensor and the negative-pressure source.

5. The apparatus of claim 1, wherein the controller is further configured to periodically couple the pressure sensor to the negative-pressure source and the distribution component through the control valve.

6. The apparatus of claim 1, wherein:
   the control valve is configured to be normally open between the pressure sensor and the distribution component; and
   the control valve is configured to be normally closed between the pressure sensor and the negative-pressure source.

7. The apparatus of claim 1, wherein:
   the control valve is configured to be normally open between the pressure sensor and the distribution component;
   the control valve is configured to be normally closed between the pressure sensor and the negative-pressure source; and
   the controller is configured to periodically switch the control valve.

8. The apparatus of claim 7, wherein switching the control valve comprises:
   closing the control valve between the pressure sensor and the distribution component; and
   opening the control valve between the pressure sensor and the negative-pressure source.

9. The apparatus of claim 1, wherein:
   the control valve is configured to be normally open between the pressure sensor and the distribution component;
   the control valve is configured to be normally closed between the pressure sensor and the negative-pressure source; and
   the controller is configured to actuate the control valve periodically to couple the pressure sensor to the negative-pressure source and the distribution component through the control valve.

10. The apparatus of claim 1, wherein the control valve comprises:
    a first inlet port configured to be fluidly coupled to the distribution component; and a second inlet port fluidly coupled to the negative-pressure source.

11. The apparatus of claim 1, wherein the control valve comprises:
a first inlet port configured to be fluidly coupled to the distribution component;
a first outlet port fluidly coupled to the first inlet port and to the pressure sensor;
a second inlet port fluidly coupled to the negative-pressure source; and
a second outlet port fluidly coupled to the second inlet port and to the pressure sensor.

12. The apparatus of claim 1, wherein the control valve comprises:
a first valve configured to be fluidly coupled to the distribution component and to the pressure sensor; and
a second valve fluidly coupled to the negative-pressure source and to the pressure sensor.

13. The apparatus of claim 12, wherein:
the first valve is an electromechanical valve having two positions and comprising a first inlet port, a first outlet port, and an exhaust port;
the first inlet port is configured to be fluidly coupled to the distribution component;
the first outlet port is fluidly coupled to the pressure sensor;
the first valve is normally open between the first inlet port and the first outlet port;
the second valve is an electromechanical valve having two positions and comprising a second inlet port and a second outlet port;
the second inlet port is fluidly coupled to the negative-pressure source;
the second outlet port is fluidly coupled to the pressure sensor; and
the second valve is normally closed between the second inlet port and the second outlet port.

14. The apparatus of claim 12, wherein:
the first valve is an electromechanical valve comprising a first inlet port, a first outlet port, and a first fluid path;
the first inlet port is configured to be fluidly coupled to the distribution component;
the first outlet port is fluidly coupled to the pressure sensor;
the first fluid path is normally open between the first inlet port and the first outlet port;
the second valve is an electromechanical valve comprising a second inlet port, a second outlet port, and a second fluid path;
the second inlet port is fluidly coupled to the negative-pressure source;
the second outlet port is fluidly coupled to the pressure sensor;
the second fluid path is normally closed between the second inlet port and the second outlet port; and
the controller is configured to:
actuate the first valve to close the first fluid path between the first inlet port and the first outlet port; and
actuate the second valve to open the second fluid path between the second inlet port and the second outlet port.

15. The apparatus of claim 12, wherein:
the first valve is an electromechanical valve comprising a first inlet port, a first outlet port, an exhaust port, and a first fluid path;
the first inlet port is configured to be fluidly coupled to the distribution component;
the first outlet port is fluidly coupled to the pressure sensor;
the first fluid path is normally open between the first inlet port and the first outlet port;
the second valve is an electromechanical valve comprising a second inlet port, a second outlet port, and a second fluid path;
the second inlet port is fluidly coupled to the negative-pressure source;
the second outlet port is fluidly coupled to the pressure sensor;
the second fluid path is normally closed between the second inlet port and the second outlet port; and
the controller is configured to:
actuate the first valve to close the first fluid path between the first inlet port and the second inlet port, and open the first fluid path between the first inlet port and the exhaust port; and
actuate the second valve to open the second fluid path between the second inlet port and the second outlet port.

16. The apparatus of claim 1, wherein:
the control valve is an electromechanical valve comprising:
a first inlet port configured to be fluidly coupled to the distribution component;
a first outlet port fluidly coupled to the first inlet port and to the pressure sensor;
a first fluid path normally open between the first inlet port and the first outlet port;
a second inlet port fluidly coupled to the negative-pressure source;
a second outlet port fluidly coupled to the second inlet port and to the pressure sensor; and
a second fluid path normally open between the second inlet port and the second outlet port; and
the controller is configured to:
actuate the control valve to fluidly couple the first inlet port to the second outlet port and to fluidly couple the second inlet port to the first outlet port.

17. The apparatus of claim 1, further comprising an electric sensor coupled to the negative-pressure source and to the controller.

18. The apparatus of claim 1, wherein the control valve is a solenoid valve.

19. The apparatus of claim 1, wherein the distribution component is a tissue interface.

20. The apparatus of claim 1, further comprising a fluid container fluidly coupled to the negative-pressure source and configured to be fluidly coupled to the distribution component.

21. An apparatus for providing negative-pressure therapy, the apparatus comprising:
a negative-pressure source;
a pressure sensor;
a control valve;
a first feedback path configured to pneumatically couple the pressure sensor to a distribution component through the control valve;
a second feedback path configured to pneumatically couple the pressure sensor to the negative-pressure source through the control valve;
wherein the control valve is configured to selectively couple the pressure sensor to the first feedback path and to selectively couple the pressure sensor to the second feedback path; and a controller coupled to the negative-pressure source, the control valve, and the pressure sensor, the controller configured to:
actuate the control valve;
sample a signal from the pressure sensor, the signal indicative of pressure measured by the pressure sensor; and
operate the negative-pressure source based on the signal.

22. The apparatus of claim 21, wherein the controller is further configured to vent the first feedback path through the control valve.

23. The apparatus of claim 21, wherein the controller is further configured to actuate the control valve to merge the first feedback path and the second feedback path.

24. The apparatus of claim 21, wherein the controller is further configured to diagnose an operating condition based on the signal and activate an alert indicative of the operating condition.

25. The apparatus of claim 21, wherein operating the negative-pressure source comprises comparing the signal to a set-point and driving the negative-pressure source to the set-point based on the comparison.

26. The apparatus of claim 21, wherein:
the control valve has a first position and a second position;
the first position couples the pressure sensor to the first feedback path;
the second position couples the pressure sensor to the second feedback path;
the signal comprises a distribution signal if the control valve is in the first position and a supply signal if the control valve is in the second position; and
the controller is configured to:
periodically switch the control valve from the first position to the second position and sample the supply signal;
compare the supply signal to the distribution signal;
diagnose an operating condition based on the comparison; and
activate an alert based on the operating condition.

27. The apparatus of claim 21, wherein:
the pressure sensor is pneumatically coupled to the first feedback path;
the control valve has a first position and a second position;
the first position closes the second feedback path between the pressure sensor and the negative-pressure source;
the second position opens the second feedback path between the pressure sensor the negative-pressure source;

the signal comprises a distribution signal if the control valve is in the first position and a performance signal if the control valve is in the second position; and
the controller is configured to:
sample the distribution signal;
periodically switch the control valve from the first position to the second position and sample the performance signal;
compare the performance signal to the distribution signal;
diagnose an operating condition based on the comparison; and
activate an alert based on the operating condition.

28. The apparatus of claim 21, further comprising an electric sensor coupled to the negative-pressure source.

29. The apparatus of claim 28, wherein:
the control valve has a first position and a second position;
the first position couples the pressure sensor to the first feedback path;
the second position couples the pressure sensor to the second feedback path;
the signal comprises a distribution signal if the control valve is in the first position and a supply signal if the control valve is in the second position; and
the controller is configured to:
periodically switch the control valve from the first position to the second position and sample the supply signal;
sample a power signal from the electric sensor;
compare a responsiveness at least one of the distribution signal and the supply signal to a change in the power signal;
diagnose an operating condition based on the comparison; and
activate an alert based on the operating condition.

30. The apparatus of claim 21, wherein the distribution component is a tissue interface.

31. The apparatus of claim 21, wherein the distribution component is a fluid container.

32. A method for controlling negative-pressure treatment, the method comprising:
sampling a signal from a pressure sensor coupled to a first feedback path through a control valve and indicative of an operating parameter measured by the pressure sensor;
periodically operating the control valve to couple the pressure sensor to a second feedback path through the control valve and switch the operating parameter measured by the pressure sensor; and
operating a negative-pressure source based on the signal.

* * * * *